(12) United States Patent
Bruemmer et al.

(10) Patent No.: US 9,033,530 B2
(45) Date of Patent: May 19, 2015

(54) PHOSPHOR DEVICE AND LIGHTING APPARATUS COMPRISING THE SAME

(75) Inventors: Matthias Bruemmer, Wusterwitz (DE); Matthias Morkel, Berlin (DE)

(73) Assignee: OSRAM GmbH, Munich (DE)

( * ) Notice: Subject to any disclaimer, the term of this patent is extended or adjusted under 35 U.S.C. 154(b) by 0 days.

(21) Appl. No.: 13/805,777

(22) PCT Filed: Jun. 22, 2010

(86) PCT No.: PCT/EP2010/058813
§ 371 (c)(1),
(2), (4) Date: Dec. 20, 2012

(87) PCT Pub. No.: WO2011/160676
PCT Pub. Date: Dec. 29, 2011

(65) Prior Publication Data
US 2013/0094181 A1    Apr. 18, 2013

(51) Int. Cl.
| F21V 9/16 | (2006.01) |
|---|---|
| F21K 2/00 | (2006.01) |
| A61B 1/06 | (2006.01) |
| G03B 21/20 | (2006.01) |
| H04N 9/31 | (2006.01) |
| B32B 3/26 | (2006.01) |
| F25B 21/02 | (2006.01) |
| F25D 17/06 | (2006.01) |

(52) U.S. Cl.
CPC .............. *F21K 2/00* (2013.01); *A61B 1/0653* (2013.01); *G03B 21/204* (2013.01); *H04N 9/315* (2013.01); *B32B 3/263* (2013.01); *F21V 9/16* (2013.01); *F25B 21/02* (2013.01); *F25D 17/06* (2013.01)

(58) Field of Classification Search
CPC .. F21Y 2101/02; H04N 9/3197; G02B 27/20; F21W 2131/406; F21V 29/004; H01L 33/60
USPC ............ 362/84, 249.01, 249.02, 249.11, 259, 362/294, 327, 328, 373, 800, 812; 250/472.1, 483.1, 484.4, 486.1, 487.1, 250/493.1, 494.1, 603.1; 257/98–100, 257/E33.071–E33.073; 353/31; 313/112–114, 502, 506, 512
See application file for complete search history.

(56) References Cited

U.S. PATENT DOCUMENTS

| 7,382,091 | B2 * | 6/2008 | Chen et al. | 313/512 |
|---|---|---|---|---|
| 7,663,152 | B2 * | 2/2010 | Bierhuizen et al. | 257/98 |
| 7,675,079 | B1 * | 3/2010 | Kley | 257/98 |
| 7,800,287 | B2 * | 9/2010 | Zheng et al. | 313/112 |
| 8,044,418 | B2 * | 10/2011 | Loh et al. | 257/98 |

(Continued)

FOREIGN PATENT DOCUMENTS

| CN | 1426604 | 6/2003 |
|---|---|---|
| CN | 1600025 | 3/2005 |

(Continued)

*Primary Examiner* — Hargobind S Sawhney
(74) *Attorney, Agent, or Firm* — Cozen O'Connor

(57) ABSTRACT

A phosphor device comprising a carrier member having upper and lower faces; a reflecting member having a side surface portion and a bottom portion, the reflecting member being arranged at the upper face of the carrier member; a phosphor layer being embedded in the reflecting member; a transmitting member having a first end face and a second end face, the transmitting member being arranged on the phosphor layer, wherein the first end face of the transmitting member completely covers the top portion of the phosphor layer.

12 Claims, 2 Drawing Sheets

(56) References Cited

U.S. PATENT DOCUMENTS

| | | | |
|---|---|---|---|
| 8,053,799 B2 * | 11/2011 | Kwon et al. | 257/98 |
| 8,096,668 B2 * | 1/2012 | Abu-Ageel | 362/84 |
| 8,147,081 B2 * | 4/2012 | Mrakovich et al. | 362/84 |
| 8,449,128 B2 * | 5/2013 | Ko et al. | 362/84 |
| 2008/0094835 A1 | 4/2008 | Marra et al. | |
| 2008/0291670 A1 | 11/2008 | Rains | |
| 2010/0202129 A1 * | 8/2010 | Abu-Ageel | 362/84 |
| 2010/0231863 A1 * | 9/2010 | Hikmet et al. | 353/31 |

FOREIGN PATENT DOCUMENTS

| | | |
|---|---|---|
| CN | 1993581 | 7/2007 |
| WO | WO 2008/039010 | 4/2008 |
| WO | WO 2009021859 A1 * | 2/2009 |
| WO | WO 2009/047683 | 4/2009 |
| WO | WO 2009047683 A3 * | 5/2009 |
| WO | WO 2010/067291 | 6/2010 |
| WO | WO 2010/090862 | 8/2010 |

* cited by examiner

PHOSPHOR DEVICE AND LIGHTING APPARATUS COMPRISING THE SAME

RELATED APPLICATIONS

This is a U.S. National Phase Application under 35 USC 371 of International Application PCT/EP2010/058813 filed on Jun. 22, 2010.

FIELD OF THE INVENTION

The invention relates to a phosphor device. Furthermore, the invention relates to a lighting apparatus comprising such phosphor device.

BACKGROUND OF THE INVENTION

Phosphor devices are used in lighting apparatus wherein the phosphor is remote from the exciting light source, i.e. there is no direct contact between the phosphor and the exciting light source. Therefore, they are also called remote phosphor devices. Remote phosphor devices can be used in various lighting applications, e.g. in RGB projection equipment, generating red (R), green (G) and blue (B) light for colored video projection. Other possible lighting applications comprise medical, architectural or entertainment lighting.

In prior art, remote phosphor devices, such as phosphor wheels, the phosphor is coated on a carrier plate. The phosphor is excited by exciting light, e.g. visible blue laser light (450 nm), impinging on the phosphor. The exciting laser light is wavelength-converted by the phosphor to generate light with longer wavelengths (e.g. broad spectral distribution with a peak about 520 nm for green light). Due to the physical nature of the wavelength-conversion, part of the exciting light energy is converted to heat (Stokes Loss). The greater the frequency difference between exciting and wavelength-converted light, the higher the Stokes Loss and thus the higher the thermal impact on the phosphor. Further effects, such as light absorbance, heat the phosphor additionally. The turning of the phosphor wheel facilitates removal of the heat generated in the phosphor.

The wavelength-converted light from the phosphor is gathered by a transmitting member, e.g. an optical element such as a lens made of glass, arranged in front of the phosphor wheel. Due to the turning of the phosphor wheel, a certain distance between the phosphor wheel and the transmitting member has to be kept. However, the gap causes optical losses. Firstly, there are reflection losses (Fresnel losses), because of different refractive indices of air (gap) and glass (transmitting member), which are independent of the size of the gap. Reflection losses increase with increasing angle of incidence. Secondly, the rays of the wavelength-converted light outside the acceptance angle of the transmitting member, i.e. rays which miss the entrance face of the transmitting member, are lost. Acceptance losses increase with increasing gap between phosphor surface and entrance face of the transmitting member.

SUMMARY OF THE INVENTION

It is an object of the present invention to provide a phosphor device with improved optical efficiency.

Another object of the present invention is the removal of the heat generated in the phosphor device.

The object is achieved in accordance with one aspect of the present invention, by a phosphor device comprising: a carrier member having upper and lower faces; a reflecting member having a side surface portion and a bottom portion, the reflecting member being arranged at the upper face of the carrier member; a phosphor layer being embedded in the reflecting member; a transmitting member having a first end face and a second end face, the transmitting member being arranged on the phosphor layer, whereby the first end face of the transmitting member completely covers the top portion of the phosphor layer.

Another aspect of the present invention relates to a lighting apparatus comprising the phosphor device according to an embodiment of the present invention.

According to an embodiment of the present invention, the phosphor layer, which may comprise at least one phosphor or a phosphor mixture, either in form of a powder, paste, slurry or liquid, is embedded in a reflecting member. The phosphor or phosphor mixture may be embedded by suitable techniques such as slurrying, galvanic deposition, spin coating or the like. The proper thickness of the phosphor layer depends on the composition and its absorbing properties and is typically in the range between 50 ym and 1 mm. The phosphor is designed to convert blue or UV light (e.g. 450 nm, 405 nm or shorter wavelengths) into visible light or near infra-red light with longer wavelengths than the exciting light. According to the intended application, the phosphor layer may have a suitable shape, e.g. a rectangular shape for video projection or a circular shape for endoscopy.

Furthermore, a transmitting member, which may be an optical element made of glass, e.g. quartz glass, optical glass (e.g. BK7) or acrylic glass, or a fiber bundle, completely covers the top portion of and is essentially in contact with the phosphor layer. Due to this arrangement of reflecting member, phosphor layer and transmitting member, particularly the latter completely covering the phosphor layer, the rays of the light converted by the phosphor layer are efficiently coupled into the transmitting member.

To further reduce the reflection losses for the exciting light as well as for the wavelength-converted light, the transmitting member may essentially be in direct contact with the top portion of the phosphor layer, thereby reducing the gap between the top portion of the phosphor layer and the transmitting member as much as possible.

To even further reduce the optical losses, the essentially direct contact may be supported by an immersion layer between the first end face of the transmitting member and the top portion of the phosphor layer. The immersion layer may consist of a liquid or a solid immersion material. The index of refraction of the immersion material is preferably less than the index of refraction of the transmitting member.

Another important aspect for improving the optical efficiency of the phosphor device is the embedding of the phosphor layer into the reflecting member. The bottom portion as well as the side surface portion of the reflecting member reflect wavelength-converted light rays back thereby increasing the optical efficiency of the phosphor device. Therefore, it is preferred that at least the bottom portion of the reflecting member has a reflective surface. The reflective surface may be polished or coated with a highly reflective layer. The reflectivity of the reflective surfaces is preferably more than 75%, better more than 80% or even more than 90%. It is particularly preferred that the side surface portion of the reflecting member has also a reflective surface. This improves the optical efficiency significantly over phosphor devices with plane plates coated with phosphor layers. Under ideal conditions, the required thickness of the phosphor for completely converting the exciting light can be reduced to half the thickness required without reflecting surfaces. This reduction in turn improves the cooling of the phosphor, because the thermal resistance of the phosphor layer decreases with decreasing layer thickness.

To further improve the heat removal from the phosphor layer, it is in thermally conductive contact with the carrier member. Preferably, the carrier member is made from a material with suitable cooling properties, e.g. a metal such as copper, aluminum or the like, facilitating dissipation of the heat generated by the exciting light when impinging on the phosphor layer.

For this purpose, the reflecting member may be recessed in the top face of the carrier member. The depth of the recess may be either equal to the thickness of the phosphor layer, i.e. when embedded into the recess, the top portion of the phosphor layer is flush with the edges of the recess. Or the depth of the recess may exceed the thickness of the phosphor layer, i.e. the phosphor layer ends below the edges of the recess. In the latter case, the transmitting member extends into the recess, i.e. into the reflecting member, in order to directly contact the top portion of the embedded phosphor layer.

In an alternate embodiment, the reflecting member protrudes at least partially from the top face of the carrier member. This means that the side surface portion of the reflecting member is formed by the inner face of an enclosure protruding from the top face of the carrier member.

In any case, the reflecting member may be an integral part of the carrier member or a separate part connected with the carrier member. It may be advantageous, for instance, to first coat the reflecting front face of a metal support with the phosphor layer and then mounting the coated bar into a suitable recess of the carrier member.

The area of the first end face of the transmitting member, which is in contact with the top portion of the phosphor layer, is at least the same as the area of the top portion of the phosphor layer thus covering the complete area of the phosphor surface layer. It may even exceed the top portion of the phosphor layer, except for the case that the transmitting member extends into the reflecting member. In any case, the complete covering of the top portion of the phosphor layer by the transmitting member is advantageous, because the phosphor is safely contained in the device even if it is a slurry or liquid. Furthermore, the phosphor is safe from corrosive environments or humidity if sealed in a proper manner.

Furthermore, according to an embodiment of the present invention, the phosphor device may comprise a cooling member. The cooling member may be a solid block made from a material with suitable cooling properties, e.g. a metal such as copper, aluminum, aluminum alloy or the like. Furthermore, the cooling member may comprise a heat sink with cooling fins. In addition, the cooling member may comprise a vapor chamber, which assists cooling by way of evaporation. In an alternate embodiment, the cooling member may comprise an active cooling device, particularly a forced air cooling, a liquid cooling or a thermoelectric cooling device, e.g. a Peltier cooling device. The cooling member may also function as the carrier member. In other words, in this case, the cooling member and the carrier member may be a one-piece structural element. Alternatively, the cooling member and the carrier member may be separate structural elements.

BRIEF DESCRIPTION OF THE DRAWINGS

Embodiments of the present invention will now be described, by way of example, with reference to the accompanying drawings in which.

DETAILED DESCRIPTION OF THE DRAWINGS

Figure 1A:
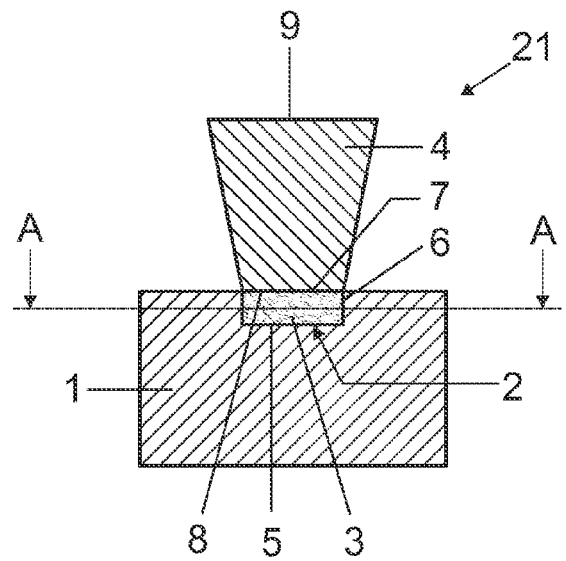
FIG. 1a is a cross-sectional side view of an embodiment of a phosphor device according to the present invention.

In the attached drawings, showing different embodiments of the present invention, the same reference numerals are used for the same or similar features.

Figure 1B:
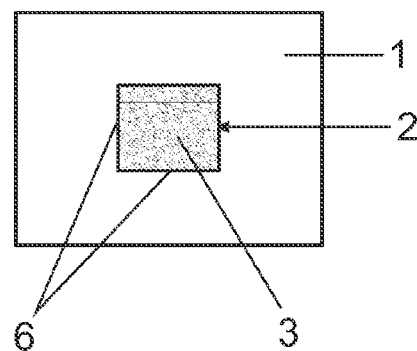
FIG. 1b is a cross-sectional view of the embodiment shown in FIG. 1a across the line AA.

As schematically shown in FIGS. 1a and 1b, a first embodiment of a phosphor device 21 is constructed having a carrier member 1 made of aluminum, a reflecting member 2, recessed in the carrier member 1, a phosphor layer 3, embedded in the reflecting member 2, and a transmitting member 4 made of optical glass, preferably quartz glass or BK7 (index of refraction is 1.46 and 1.52 respectively), arranged on the top portion of the phosphor layer 3. Due to the good cooling properties of aluminum, the carrier member 1 also functions as a cooling member. The recessed reflecting member 2 is shaped into the upper face of the carrier member 1. The recess has a rectangular bottom portion 5 of about 1.6×1.2 mm$^2$. If an immersion layer is used, both lengths are reduced (divided by the index of refraction of the immersion layer). The depth of the side surface portion 6 depends on the absorbance and scattering properties of the phosphor and immersion layer to be embedded into the reflecting member. Typical values for the thickness of the phosphor layer and immersion layer are approximately 0.5 mm and 0.1 mm, respectively. After shaping the recess, the bottom portion 5 as well as the side surface portion 6 are polished to enhance the reflectivity of the recessed reflecting member 2. The phosphor layer 3 is made of a single component phosphor to generate light of a desired color (preferred: red, green or blue). Alternatively, a multi-component phosphor, e.g. a mixture of three different types of phosphor components, may be used resulting in the emission of white light when excited by a suitable exciting light source. The at least one phosphor compo-nent or phosphor mixture is filled into the recess to form a phosphor layer 3 until the top portion 7 of the phosphor layer 3 is flush with the top face of the carrier member 1. A first end face 8 of the transmitting member 4 equals the top portion of the phosphor layer 3 and is in close contact with the latter. Due to this arrangement, optical losses are small. They may be further reduced by virtue of an immersion agent, e.g. silicone arranged between the top portion of the phosphor layer 3 and the first end face 8 of the transmitting member 4. Silicon has an index of refraction of about 1.42, which is lower than the one of the transmitting member. Although a direct index match would optimally reduce the Fresnel losses, the lower value is preferred, because the light rays are refracted towards the optical axis, thus enhancing the transmittance efficiency of the transmitting member. The transmitting member is tapered, the second end face 9 being larger than the first end face 8.

The whole setup is designed for projection purposes illuminating a 0.55" digital mirror device (DMD, also known as Digital Light Processing Unit—DLP®—by Texas Instruments). Therefore, the wavelength-converted light leaving the transmitting member should have an angular distribution of below 12°. This is accomplished by the conical transmitting member. The size of the other end face of the transmitting member is then determined according to the Etendue preservation theorem, resulting in 11.2×8.4 mm².

Figure 2:
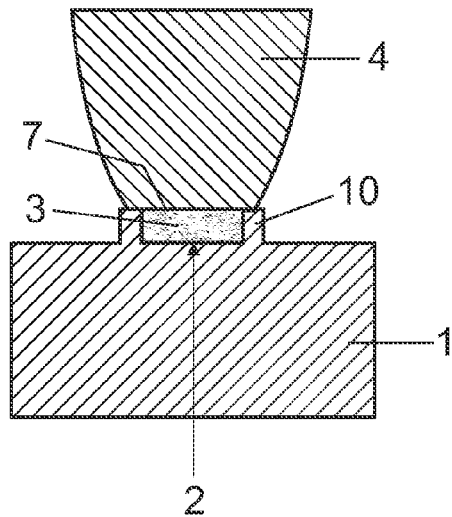
FIG. 2 is a cross-sectional side view of another embodiment of a phosphor device according to the present invention.

An alternate embodiment of the phosphor device is shown in FIG. 2. It differs from the first embodiment shown in FIGS. 1a, 1b only in that the reflecting member 2 is not recessed in the top face of the carrier member 1 but pro-trudes from it. Therefore, the side surface portion of the reflecting member 2 is formed by the inner face of an enclosure 10 protruding from the top face of the carrier member. The enclosure 10 is filled flush with a phosphor mixture, thus forming a phosphor layer 3. The first end face 7 of the tapered transmitting member 4 is in direct contact with the top portion of the phosphor layer 3. In this embodiment, the area of the first end face 7 of the tapered transmitting member 4 exceeds the area of the top portion of the phosphor layer 3 slightly. However, the area of the first end face 7 of the tapered transmitting member 4 could as well just cover the top portion of the phosphor layer 3, similar to the embodiment shown in FIGS. 1a, 1b. Furthermore, the edges of the transmitting member 4 are formed as Bezier curves instead of straight lines, thereby improving the acceptance angle for the wavelength-converted light. Alternatively, the transmitting member 4 may be segmented to approximate Bezier curved edges.

Figure 3:
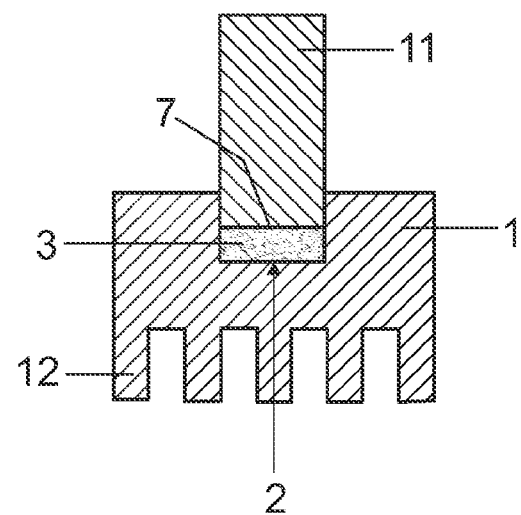
FIG. 3 is a cross-sectional side view of another embodiment of a phosphor device according to the present invention.

The alternate embodiment shown in FIG. 3 differs from the first embodiment shown in FIGS. 1a, 1b mainly in that the recess for the reflecting member 2 is significantly deeper than the thickness of the phosphor layer 3. Furthermore, cooling fins 12 are formed at the lower face of the carrier member 1 to improve heat removal. The transmitting member 11 extends into the recess to ensure that the first end face 7 of the transmitting member 11 is in contact with the top portion of the phosphor layer 3. For the sake of simplicity, the transmitting member 11 is not tapered. However, a tapered transmitting member 11 could also be used if appropriate by tapering the upper part of the recess above the phosphor layer 3. Alternatively, the part of the transmitting member inside the recess may be straight and only the part outside of the recess may be tapered.

Figure 4:
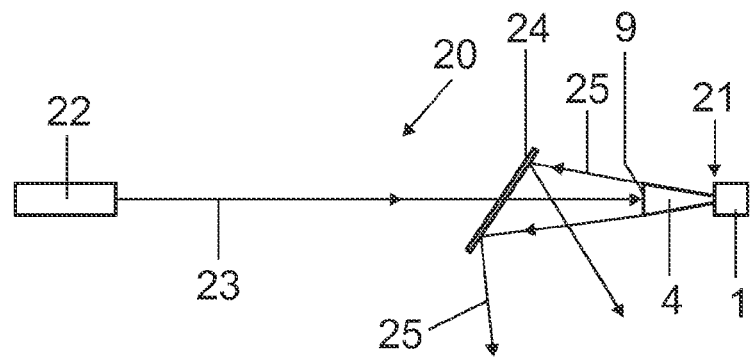
FIG. 4 is a schematic view of a lighting apparatus comprising a phosphor device according to an embodiment of the present invention.

FIG. 4 shows a schematic view of a lighting apparatus 20 comprising a phosphor device 21 as shown in FIGS. 1a, 1b. The lighting apparatus 20 may be used for projection applications. The lighting apparatus 20 further comprises at least one laser diode 22, emitting exciting light 23 of a wavelength of about 450 nm, and a dichroitic mirror 24 arranged on the optical axis between the laser diodes 22 and the phosphor device 21. The exciting light 23 passes through the dichroitic mirror 24, enters the phosphor device 21 through the second end face 9 of the transmitting member 4 and is received by the phosphor layer (not shown) embedded in the carrier member 1. The phosphor layer consists of a phosphor converting the exciting laser light (450 nm) into the desired wavelength-converted light. Typical phosphors for wavelength-conversion are Ce doped YAG and Eu doped YAG for green and red, respectively. The wavelength-converted light 25 generated by the phosphor layer is gathered by the transmitting member 4 and transmitted to the dichroitic mirror 24. The dichroitic mirror 24 is tilted to reflect the wavelength-converted light off the optical axis defined by the beam of the diode laser 22.

Figure 5:
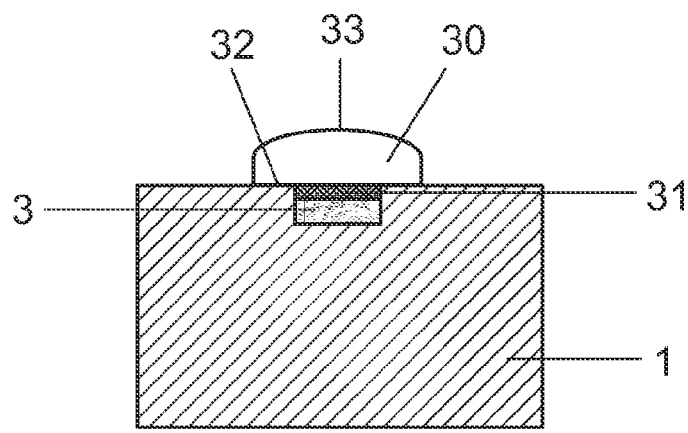
FIG. 5 is a cross-sectional side view of another embodiment of a phosphor device according to the present invention.

An alternate embodiment of the phosphor device is shown in FIG. 5. It differs from the first embodiment shown in FIGS. 1a, 1b in that the phosphor layer 3 has a circular shape and, therefore, the transmitting member 30 is shaped as a circular lens. Furthermore, the depth of the recess is dimensioned for covering not only the phosphor layer 3 but also an immersion layer 31 on top of the former. The lens 30 has a flat face 32, which is in contact with the flat upper face of the carrier member 1. The area of the flat face 32 of the lens 30 extends beyond the area of the phosphor layer 3 for the sake of practicability, thus covering the entire phosphor surface layer. The immersion layer 31 fills the gap between the top portion of the phosphor layer 3 and the corresponding area of the flat face 32 of the lens 3. The other face 33 of the lens 30 is convex.

Any other combinations of the various features disclosed in the above embodiments may be appropriate as the case arises.

The scope of protection of the invention is not limited to the examples given hereinabove. The invention is embodied in each novel characteristic and each combination of characteristics, which includes every combination of any features which are stated in the claims, even if this feature or combination of features is not explicitly stated in the examples.

The invention claimed is:

1. A lighting apparatus comprising:
   a phosphor device; and
   an exciting light source that emits exciting light, the exciting light source arranged outside of the phosphor device;
   wherein the phosphor device comprises:
      a carrier member having upper and lower faces;
      a reflecting member having a side surface portion and a bottom portion, the reflecting member being arranged at the upper face of the carrier member;
      a phosphor layer being embedded in the reflecting member; and
      a transmitting member having a first end face and a second end face, the transmitting member being arranged on the phosphor layer, wherein the first end face of the transmitting member completely covers the top portion of the phosphor layer; and
   wherein the first end face of the transmitting member is in substantially direct contact with the top portion of the phosphor layer,
   wherein the phosphor layer receives the exciting light entering the phosphor device through the second end face of the transmitting device to generate a wavelength-converted light.

2. The lighting apparatus according to claim 1, wherein the reflecting member is recessed in the top face of the carrier member.

3. The lighting apparatus according to claim 1, wherein the area of the first end face of the transmitting member exceeds the area of the top portion of the phosphor layer.

4. The lighting apparatus according to claim 1, wherein at least the bottom portion of the reflecting member has a reflective surface.

5. The lighting apparatus according to claim 1, wherein the phosphor layer comprises at least one phosphor or a phosphor mixture.

6. The lighting apparatus phosphor device according to claim 5, wherein the cooling member comprises a vapor chamber.

7. The lighting apparatus phosphor device according to claim 1, wherein the carrier member comprises a cooling member.

8. The lighting apparatus phosphor device according to claim 5, wherein the cooling member comprises an active cooling device, particularly a forced air cooling, a liquid cooling or a thermoelectric cooling device.

9. The lighting apparatus according to claim 1, wherein the exciting light source comprises a laser light source.

10. A lighting apparatus comprising:
    a phosphor device; and
    an exciting light source that emits exciting light, the exciting light source arranged outside of the phosphor device,
    wherein the phosphor device comprises:

a carrier member having upper and lower faces;

a reflecting member having a side surface portion and a bottom portion, the reflecting member being arranged at the upper face of the carrier member;

a phosphor layer being embedded in the reflecting member;

a transmitting member having a first end face and a second end face, and an immersion layer between the first end face of the transmitting member and the top portion of the phosphor unit wherein the transmitting member is arranged on the phosphor layer, wherein the first end face of the transmitting member completely covers the top portion of the phosphor layer; and wherein the phosphor layer receives the exciting light entering the phosphor device through the second end face of the transmitting device to generate a wavelength-converted light.

11. A lighting apparatus comprising:

a phosphor device; and an exciting light source that emits exciting light, the exciting light source arranged outside of the phosphor device, wherein the phosphor device comprises:

a carrier member having upper and lower faces;

a reflecting member having a side surface portion and a bottom portion, the reflecting member being arranged at the upper face of the carrier member;

a phosphor layer being embedded in the reflecting member; and a transmitting member having a first end face and a second end face, the transmitting member being arranged on the phosphor layer, wherein the first end face of the transmitting member completely covers the top portion of the phosphor layer; and wherein the first end face of the transmitting member is in substantially direct contact with the top portion of the phosphor layer, wherein the phosphor layer receives the exciting light entering the phosphor device through the second end face of the transmitting device to generate a wavelength-converted light, wherein the reflecting member is recessed in the top face of the carrier member, wherein the recess for the reflecting member is significantly deeper than the thickness of the phosphor layer and wherein the transmitting member extends into the recess to ensure that the first end face of the transmitting member is in contact with the top portion of the phosphor layer.

12. The lighting apparatus phosphor device according to claim 11, wherein the at least one phosphor or phosphor mixture is a powder, a paste, a slurry or a liquid.

* * * * *